(12) United States Patent
Graves et al.

(10) Patent No.: US 9,333,022 B2
(45) Date of Patent: May 10, 2016

(54) TOOL FOR EXTRACTING A PIN

(75) Inventors: William Graves, Melbourne (AU); Iain Alexander McMillan, Christchurch (NZ); Ray Randle, Tugun (AU)

(73) Assignee: DEPUY INTERNATIONAL LIMITED, Leeds (GB)

( * ) Notice: Subject to any disclaimer, the term of this patent is extended or adjusted under 35 U.S.C. 154(b) by 1228 days.

(21) Appl. No.: 12/375,169

(22) PCT Filed: Jul. 5, 2007

(86) PCT No.: PCT/GB2007/002498
§ 371 (c)(1),
(2), (4) Date: May 25, 2010

(87) PCT Pub. No.: WO2008/012496
PCT Pub. Date: Jan. 31, 2008

(65) Prior Publication Data
US 2010/0234851 A1    Sep. 16, 2010

(30) Foreign Application Priority Data

Jul. 26, 2006    (GB) .................................. 0614820.9

(51) Int. Cl.
*A61B 17/58* (2006.01)
*A61B 17/60* (2006.01)
*A61F 2/00* (2006.01)
*A61B 17/92* (2006.01)

(52) U.S. Cl.
CPC ............... *A61B 17/92* (2013.01); *Y10T 29/539* (2015.01)

(58) Field of Classification Search
CPC ........... A61B 17/8875; A61B 17/0401; A61B 2017/0409
USPC ......................................................... 606/104
See application file for complete search history.

(56) References Cited

U.S. PATENT DOCUMENTS 4,028,790 A     6/1977    Dupuis
4,627,420 A  * 12/1986    Katz .................................. 600/7

(Continued)

FOREIGN PATENT DOCUMENTS

EP    2043538    4/2009
JP    30-7300    5/1955

(Continued)

OTHER PUBLICATIONS

PCT Written Opinion, 5 pages.

(Continued)

*Primary Examiner* — Sameh Boles

(57) ABSTRACT

A tool for extracting a pin from a substrate comprises a first lever arm with a body part having a cavity in which the free end of a pin can be received, and a second lever arm which can pivot relative to the first lever arm. A jaw component is provided within the body part which can be actuated from an unlocked position in which a pin within the jaw component can slide freely past the jaw component, and a locked position in which the pin is gripped by engagement of the jaw component with the side wall of the pin, and a support is provided which can slide relative to the body part, in a direction towards the substrate from which the pin is to be extracted. Initial movement of the first lever arm relative to the second lever arm causes the jaw component to be actuated from its unlocked position to its locked position so that an inserted pin is gripped by the jaw component. Continued movement of the first lever arm relative to the second lever arm causes the support to slide relative to the body part, so that an inserted pin which is gripped by the jaw component is displaced relative to the substrate.

7 Claims, 4 Drawing Sheets

(56) References Cited

U.S. PATENT DOCUMENTS

| | | | |
|---|---|---|---|
| 6,039,313 A * | 3/2000 | Baculy | 269/168 |
| 6,066,143 A | 5/2000 | Lane | |
| 6,673,078 B1 | 1/2004 | Muncie | |
| 7,189,243 B1 * | 3/2007 | Seelig et al. | 606/104 |
| 7,341,587 B2 | 3/2008 | Molz, IV et al. | |
| 7,993,349 B2 | 8/2011 | Hearn et al. | |
| 2005/0113832 A1 | 5/2005 | Molz, IV et al. | |
| 2010/0087831 A1 | 4/2010 | Marx | |
| 2010/0234851 A1 | 9/2010 | Graves et al. | |

FOREIGN PATENT DOCUMENTS

| | | | |
|---|---|---|---|
| JP | 40-32637 | | 11/1965 |
| WO | WO 96/28103 | A1 | 9/1996 |
| WO | WO 9628103 | A1 | 9/1996 |
| WO | WO 97/00648 | A1 | 1/1997 |
| WO | WO 9700648 | A1 | 1/1997 |

OTHER PUBLICATIONS

International Search Report, dated Sep. 21, 2007, 3 pages.
UK Search Report, dated Nov. 23, 2006, 1 page.
UK Search Report Dated Apr. 4, 2013, 4 Pages.
Intl Search Report for PCT GB2013053419, Dated Mar. 14, 2014, 4 Pages.
English Translation of Japanese Notification of Reasons for Refusal for Corresponding Japanese Patent Application No. 2009-521326, Dated Jun. 22, 2012, 3 Pages.

* cited by examiner

TOOL FOR EXTRACTING A PIN

This invention relates to a tool for extracting a pin.

Removal of a fastening pin from a substrate requires that the pin is gripped securely so that a removal force is transmitted reliably to the pin. Gripping a pin which has an enlarged head can be achieved reliably by engaging the head of the pin. However, when a pin does not have an enlarged head, or when it is necessary to grip the pin other than at the end where it has an enlarged head, gripping the pin requires secure engagement with the side wall of the pin.

This problem is encountered in orthopaedic surgery procedures, for example when a pin is used to mark a location on a bone, or to fasten an instrument such as a cutting guide (for example which defines a surface for a cutting step using a saw, or which defines bores for a drilling or reaming step) to a bone. The pin has to be removed from the bone after the steps involving the pin and the instruments which have been fastened to the bone by means of the pin have been completed.

U.S. Pat. No. 6,066,143 discloses an instrument which can be used to remove a fastening pin which has an enlarged head from a bone. The instrument includes an engagement member in which the pin can be received so that the head of the pin bears against a socket, and a sliding member which can slide relative to the engagement member, distally, towards the surface of the bone from which the pin is to be extracted, and then return to its initial position. The engagement and sliding members are connected to respective handles. The relative sliding motion between the engagement and sliding members results from squeezing the handles together.

The instrument disclosed in U.S. Pat. No. 6,066,143 has the disadvantage that it requires the fastening pin to have an enlarged head.

The present invention provides a tool for extracting a pin, which includes a jaw for engaging the side wall of a pin, and first and second lever arms which, when actuated, cause the pin to be gripped and then to be extracted.

Accordingly, in one aspect, the invention the invention provides a tool for extracting a pin from a substrate, which comprises:
  a. a first lever arm including a body part having a cavity configured to receive a free end of the pin;
  b. a second lever arm pivotable relative to the first lever arm;
  c. a jaw component configured to be at least partially disposed within the cavity, the jaw component having a jaw bore and being actuatable between an unlocked position, at which a pin disposed at least partially within the jaw bore can slide within the jaw bore, and a locked position, at which the first lever arm and the second lever arm are a first distance apart and a portion of the jaw component engages the pin to substantially prevent it from sliding within the jaw bore; and
  d. a support slidably attached to the body part and configured to be positioned at a first position relative to the jaw component, when the first lever arm and the second lever arm are a first distance apart, and a second distance more distal than the first position, when the first lever arm and the second lever arm are a second distance apart, the second distance being less than the first distance.

The tool of the invention has the advantage that a fixation pin can be gripped successively at different points along its length for the purpose of applying an extraction force, using a single action to effect the gripping and extraction. This can help a user when identifying an appropriate location to grip the pin to apply the extraction force. It can also facilitate extraction of a pin which has penetrated deep into a substrate, by progressively gripping the pin at different locations along its length.

The tool of the invention has the advantage that it can be used to grip a fixation pin at any chosen point along its length. It can therefore be used to grip a fixation pin which does not have an enlarged head. It can also be used to remove a fixation pin which has penetrated deep into a substrate, by progressively gripping the pin at different locations along its length.

Preferably, the tool includes a body part having a cavity formed in it, and in which the jaw component is located at least partially within the cavity and can be displaced within the cavity to cause a pin to be gripped by relative movement between the first and second lever arms.

The body part will generally have a channel formed in it for receiving the free end of a pin. The pin can slide freely in the aligned channels in the body part and the jaw component when the jaw component is in its unlocked position. Either or each of the channels in the body part and the jaw component can have an open cross-section in the form of a trough or groove, or a closed cross-section in the form of a bore. The or each channel should preferably be chosen so that the fixation pin is a close sliding fit. For example, when the tool is intended for use to remove fixation pins which have a diameter of 3.2 mm, the channel in one or each of the body part and the jaw component will be sized so that its transverse dimension (which will be its diameter when the channel is a bore with a circular cross-section) is not more than about 3.7 mm. Accordingly, the ratio of the transverse dimension of the bore to the diameter of the fixation pin is not more than about 1.2, more preferably, not more than about 1.1. Generally, the value of that ratio will be at least about 1.05. Preferably, when the tool is intended for use to remove fixation pins which have a diameter of 3.2 mm, the transverse dimension of the channel in one or each of the body part and the jaw component is at least about 3.3 mm. It will be appreciated that the tool of the invention can be used to extract pins whose transverse dimension (which will be the diameter when the pin has a circular cross-section) varies between widely spaced limits. For example, it could be used to extract pins with a diameter which is less than 2 mm, or less than 1 mm, or less than 0.5 mm. It can be used to extract pins with a diameter which is at least 3 mm, or at least 4 mm, or at least 5 mm.

Preferably, the body part is provided by the first lever arm. The jaw component can be displaced linearly within the cavity in the body part between the locked and unlocked positions. A fixation pin can then be gripped by a shearing action at the interface between the channel in the jaw component and the channel in the body part, at one or at each end of the channel in the jaw component, which will tend to exert a bending force on the pin.

The jaw component can include more than one jaw member, especially which are capable of displacement relative to one another. The fixation pin can then be gripped between the jaw members.

Preferably, the jaw component fits in the cavity in the body part such that it can be rotated within the cavity, in a plane which contains the channel in the jaw component. In this arrangement, it can be preferred for the shape of the jaw component when viewed in outline to by defined by a part of a circle. It can be particularly preferred for the jaw component to be circular. Preferably, the cavity in the body part defines a surface against which the jaw component can sit for rotation. The surface will preferably have the shape of part or all of a circle. When the jaw component is rotated between its locked and unlocked positions, a fixation pin can be gripped by a shearing action of the ends of the channel in the jaw component on the side walls of the pin, which will tend to exert a bending force on the pin.

Preferably, the jaw component includes a control arm which extends from the cavity in the body part, through which force can be applied to the jaw component to cause it to move. Movement of the control arm can be caused by movement of a lever arm. The free end of the control arm can be made to translate. Such translation can result in, for example, translation or rotation of the jaw component, or both.

Preferably, the first lever arm acts on the body part. This can be as a result of the body part being provided as part of the first lever arm. Preferably, the second lever arm acts on the jaw component. It can act on the jaw component directly, or indirectly through a linkage. Preferably, the second lever arm acts on the support. It can act on the support directly, or indirectly through a linkage.

Preferably, during the initial movement of the first lever arm relative to the second lever arm, the second lever arm pivots about the connection (direct or indirect) between it and the support. Preferably, during the continued movement of the first lever arm relative to the second lever arm, the second lever arm pivots about a connection (direct or indirect) between it and the jaw component. For example, the connection might be between the second lever arm and a linkage to the jaw component or the jaw component control arm. The position of that connection remains largely unchanged during the continued movement, apart from such small movement that results from tightening of the grip on the fixation pin, and from changes in the height of the connection due to movement of the support being constrained along a fixed axis.

Preferably, the support has an opening in the surface which faces towards the substrate through which a pin which is to be extracted can extend, and has two limbs which extend along opposite sides of the body part, and in which the second lever arm is connected to the support on each of the said limbs. The two limbs can be connected along at least part of their length so that, for example, the support is provided by a tube. The tube can have a rounded cross-section so that the limbs are then effectively provided by oppositely located arcs on opposite sides of the tube when viewed in cross-section. It will often be preferred for the support to have at least one slot extending at least part way along its length, which defines separate limbs. The connection between the second lever arm and limbs on opposite sides of the body part can help to ensure that the forces which are applied by the second lever arm to the support are approximately symmetrical across the support, so that the tendency of the tool to twist or otherwise deform during operation is minimized.

Preferably, the opening in the support surface is a hole which is closed around its periphery. However, the opening might be open at one side, in the manner of an open ended slot. The surface of the support is preferably configured so that, when force is applied through it to the surface of the substrate from which the pin is to be extracted, damage to that substrate is minimized. Accordingly, it can be preferred for the support to engage the surface of the substrate over an appreciable area in order to minimize localized application of force to the surface of the substrate.

Preferably, the body part has a cavity formed in it, and in which the jaw component is located at least partially within the cavity and can be displaced within the cavity by relative movement between the first and second lever arms.

Preferably, the jaw component includes a control arm which extends from the cavity in the body part, through which force can be applied to the jaw component to cause a pin inserted into it to be gripped. When the support has two limbs which extend along opposite sides of the body part, the control arm can extend from the body part through a slot which is provided between the limbs.

Preferably, the angle between the direction in which force is applied to the control arm to actuate the jaw component, and the direction in which force is applied to the support to cause it to slide relative to the body part, is at least about 130°, more preferably at least about 150°, especially at least about 165°. Such alignment of the gripping and pulling forces has the advantage that applying an increasing pulling force to the fixation pin causes an increasing gripping force to be applied, so that the risk of the jaw component slipping on the surface of the fixation pin as the pulling forces increase is reduced.

Preferably, the support slides relative to the body part, in use towards the surface of the substrate, the jaw component and the first lever arm during the continued movement of the first lever arm relative to the second lever arm. Preferably, the support can be displaced relative to the body part through at least about 8 mm, more preferably at least about 10 mm, especially at least about 15 mm, for example at least about 20 mm. The distance through which the support can be displaced is affected by factors which include the mechanical advantage which can be obtained from the tool, and the size of the tool.

Preferably, the lever arms are biased resiliently towards the position in which the support is retracted and the jaw component is positioned so that the pin can slide freely relative to the jaw component.

The tool will generally be made from one or more metallic materials. The choice of suitable materials will be made having regard to the intended application of the tool. When the tool is intended for use in surgery, for example in orthopaedic surgery, it will generally be preferred for the tool to be made from stainless steels such as are commonly used in the manufacture of surgical instruments.

Embodiments of the invention will now be described by way of example with reference to the accompanying drawings, in which.

Figure 1:
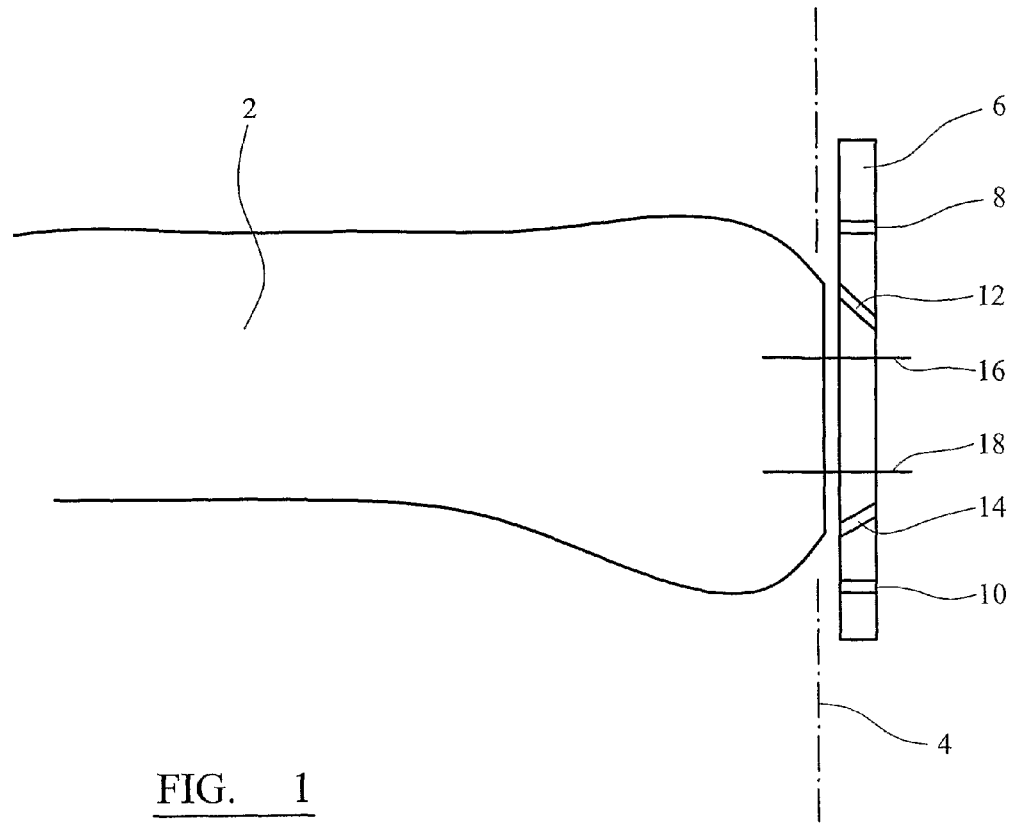
FIG. 1 is a side view of the distal end of a femur during a surgical procedure to implant a knee prosthesis, with a cutting guide block fastened to the end of the femur by means of two fixation pins.

Referring to the drawings, FIG. 1 shows schematically the distal portion of a femur 2 which is being prepared for implantation of the femoral component of a knee joint prosthesis. An initial distal cut has been performed on the femur on a resection plane 4. A cutting block fix is in place against the resected femur. The cutting block has slots 8, 10, 12, 14 to define the planes of the anterior cut, the posterior cut, the anterior chamfer cut, and the posterior chamfer cut respectively. The cutting block 6 is held in place by means of two fixation pins 16, 18 which pass through respective bores in the cutting block. The appropriate location of the cutting block on the resected femur can be located using existing techniques, for example with reference to an intra-medullary alignment rod.

After performing the cutting steps using the cutting block 6, the block can be removed from the femur to allow access to the resected femur for subsequent stages in the procedure. When the fixation pins 16, 18 are parallel, and do not have enlarged heads at their free ends, the cutting block 6 can be removed from the resected femur by sliding it over the pins.

Figure 2:
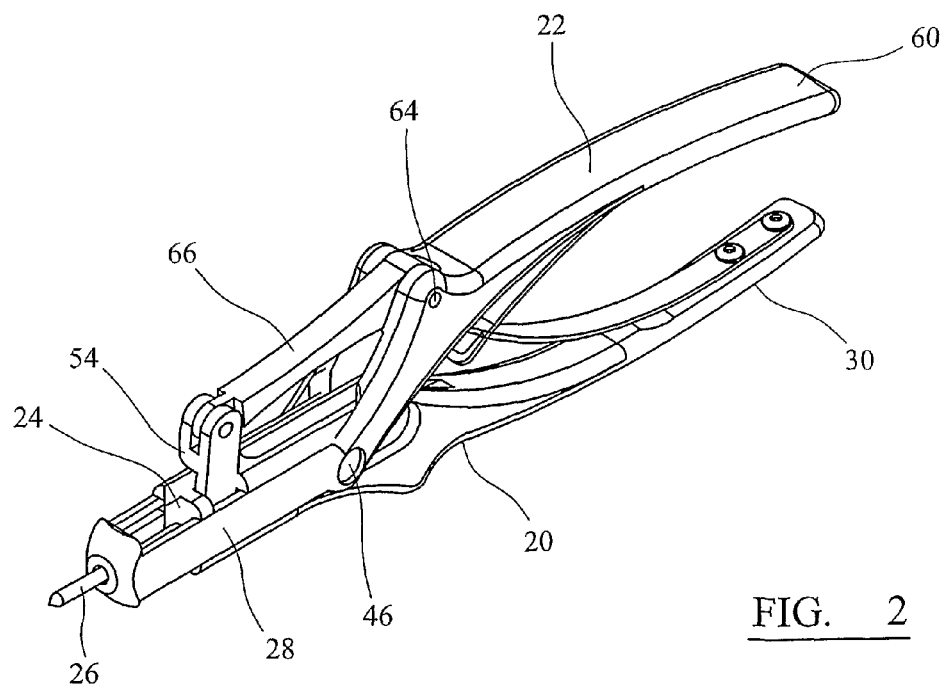
FIG. 2 is an isometric view of a tool for extracting a fixation pin according to the present invention.

The present invention addresses the removal of the fixation pins 16, 18. FIG. 2 shows a tool for extracting fixation pins according to the present invention. It comprises a first lever arm 20 and a second lever arm 22. The second lever arm is connected indirectly by means of linkages (described in more detail below) to the first lever arm so that the second lever arm can pivot relative to the first lever arm.

The first lever arm includes a body part 24 having a cavity formed in it. A jaw component is located in the cavity, which can be displaced within the cavity to cause a pin 26 whose end is inserted into the cavity to be gripped when the second lever arm is moved relative to the first lever arm. A support 28 can slide relative to the body part 24 of the first lever arm, in a direction towards the substrate from which the pin 26 is to be extracted. Accordingly, relative movement between the first and second lever arms 20, 22 initially causes the jaw component within the body part to be actuated from an unlocked position to a locked position so that the inserted pin 26 is gripped by the jaw component. Continued movement of the second lever arm relative to the first lever arm causes the support to slide towards the substrate and away from the body part, so that the inserted pin which is gripped by the jaw component is displaced relative to the substrate.

Figure 3:
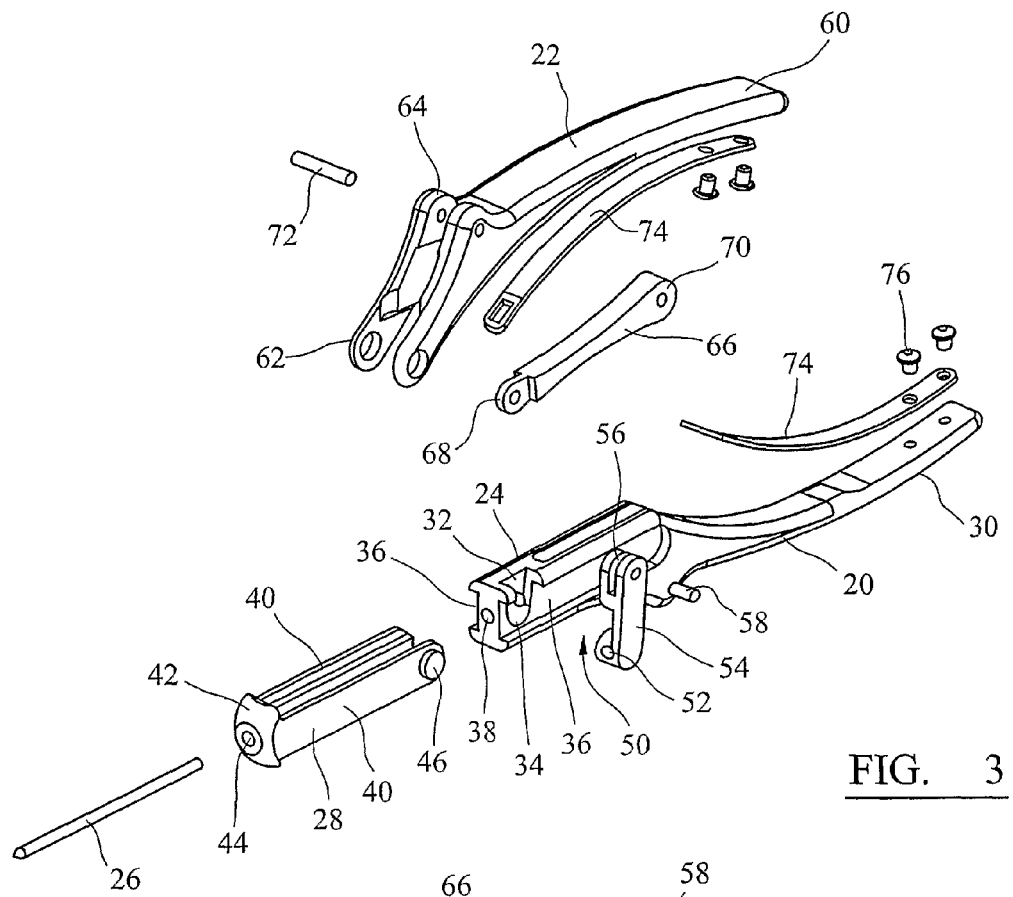
FIG. 3 is an exploded view of the tool which is shown in FIG. 2.
Figure 4:
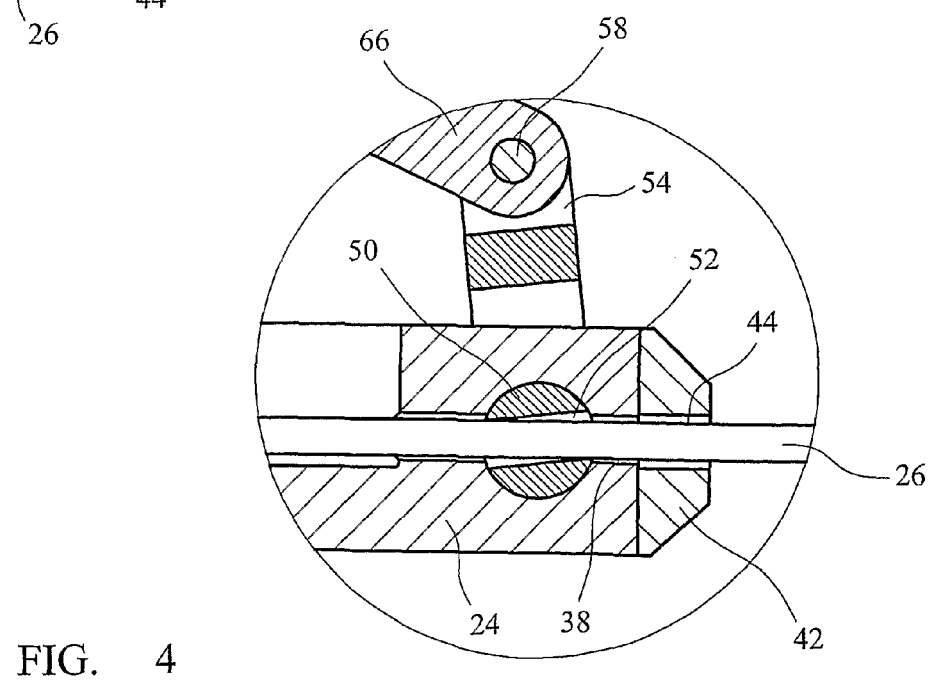
FIG. 4 is an expanded view of the jaw component for gripping a fixation pin within the tool shown in FIGS. 2 and 3.

FIG. 3 shows the components of the tool shown in FIG. 1 in more detail. The first lever arm 20 has a curved gripping section at its end opposite to the body part 24. The body part 24 has a cavity 32 formed in it with a rounded lower portion 34. The body portion has a I-shape when viewed in cross-section from one end, so that each side wall 36 defines a recess which extends along the length of the body part.

The body part has a bore 38 formed in it. The bore has a circular cross-section. The bore extends from the end of the first lever arm, and through the cavity 32.

The support 28 comprises two limbs 40 which extend generally parallel to one another, and which are interconnected at one end by means of an end wall 42. The end wall 42 of the support has a circular opening 44 formed in it. An outwardly facing spigot 46 is provided at the free end of each of the limbs. The limbs 40 are sized so that they can slide in the recesses defined by the side walls 36 of the body part of the first lever arm.

The tool includes a circular jaw component 50 which is a close fit in the cavity 32, sized so that it can rotate without excessive play in contact with the rounded part 34 of the cavity. The jaw component has a bore 52 extending through it. The bore 52 in the jaw component 50 has the same cross-sectional size and shape as the bore 38 in the body part 24 of the first lever arm 20. The bores 38, 52 can be aligned to receive the end of the fixation pin 26. A control arm 54 extends from the jaw component 50. The control arm has a pair of flanges at its free end 56 which are drilled to receive a connecting pin 58.

The second lever arm 22 has a curved portion 60 by which it can be gripped, which is located opposite to the curved portion 30 of the first lever arm when the tool is assembled.

The second lever arm 22 has a pair of aligned through holes 62 at its opposite end. These holes can receive the outwardly facing spigots 46 on the support 28, so that the second lever arm is connected to the support but can pivot relative to it.

The second lever arm has a second pair of aligned through holes 64 on its upper face. The tool includes a linkage arm 66 to interconnect the control arm 54 at its free end 56 and the second lever arm 22. The linkage arm has through holes 68, 70 at its opposite ends, for receiving fixation pins 58, 72.

Leaf spring components 74 are provided for fastening to the first and second lever arms. They are connected to the lever arms by means of fixation screws 76.

Figure 5A:
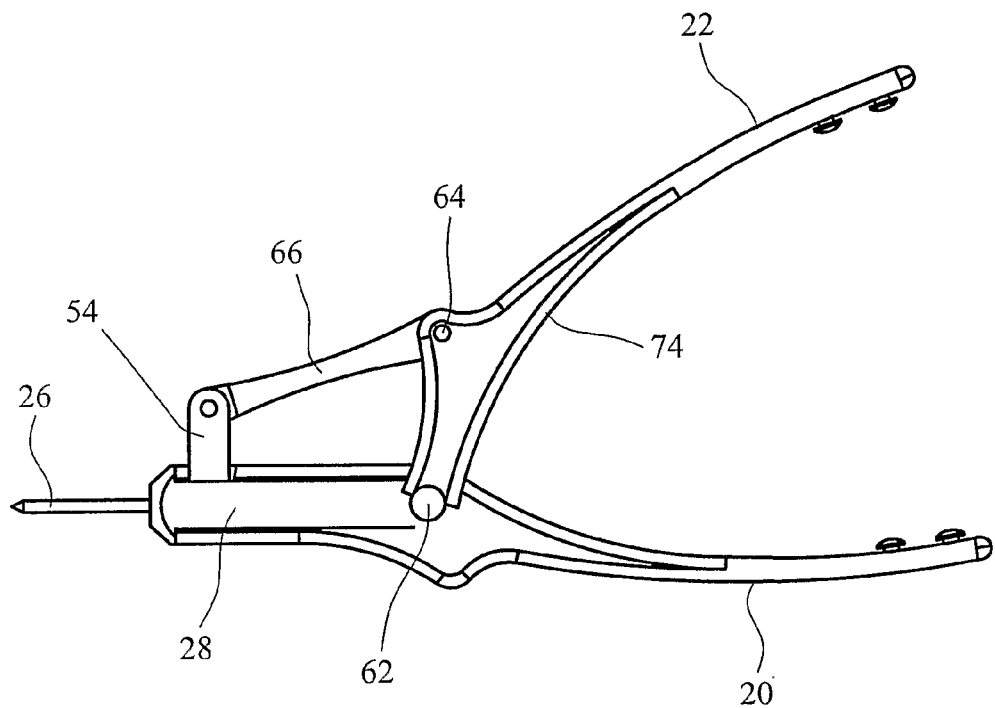
FIGS. 5A and 5B are side and sectional views respectively of the tool shown in FIG. 2, when a fixation pin is initially inserted into the tool for extraction from a substrate.
Figure 5B:
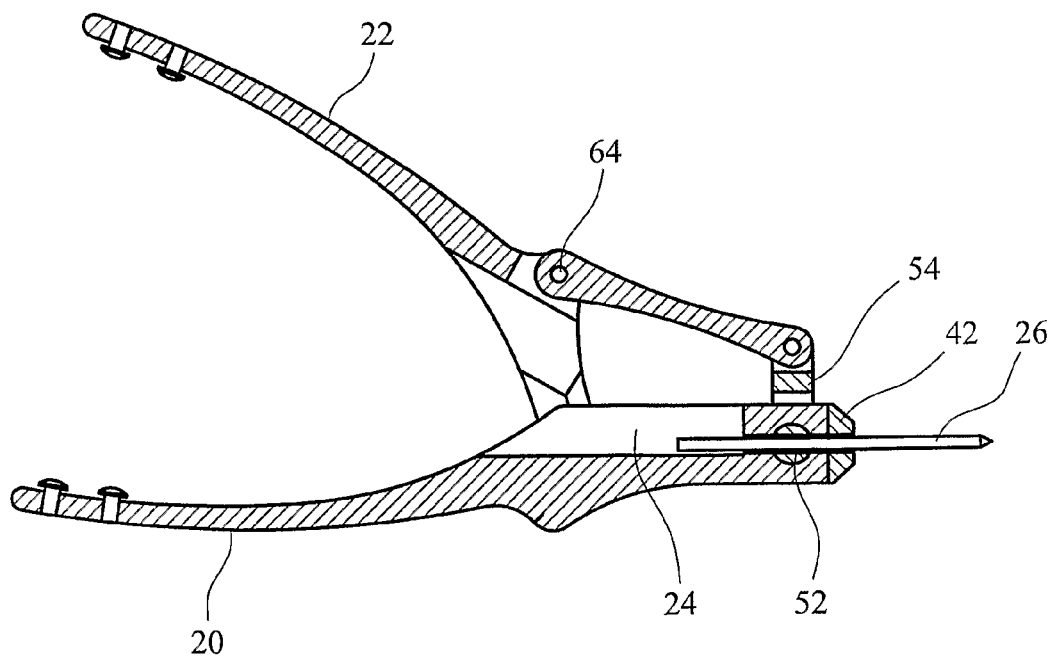

FIGS. 5 and 6 show the tool of the invention at two stages in its operation. FIGS. 5a and 5b show the tool at an initial stage in its operation. FIG. 5a is a side elevation view. FIG. 5b is a sectional elevation through the tool, rotated through 180°. As shown in FIGS. 5a and 5b, the first and second lever arms 20, 22 are biased apart by means of the springs 74. In this position, the rotational orientation of the jaw component 50 is such that the bore 52 is aligned with the bore 38 in the body part of the first lever arm. This enables the free end of the pin 26 to be inserted through the hole 44 in the end face of the support and the aligned bores.

Squeezing the first and second lever arms together initially causes the second lever arm to pivot about the through holes 62 by which it is connected to the support 28. This causes the lever arm 54 to be drawn back away from the substrate from which the pin 26 is to be extracted. This causes the jaw component 50 to rotate within the cavity 32 in the body part 24 of the first lever arm 20. The ends of the cavity 52 in the jaw component 50 impart a shearing action to the fixation pin 26, as a result of applying a localized bending force to the pin. This causes the pin to be gripped within the tool, resisting sliding in and out of the tool.

Continued squeezing together of the first and second lever arms causes the second arm to pivot about the through holes 64 at which it is connected to the linkage arm 66 and the control arm 54. The control arm tends to move very little at this stage, subject only to deformation of the pin as a result of further rotation of the jaw component 50 within the cavity 32. Accordingly, squeezing together of the first and second lever arm 20, 22 causes the support 28 to be thrust forward relative to the body part 24 of the first lever arm 30, by virtue of the connection between the second lever arm 22 and the support 28 at the through holes 62 in the second lever arm 22. It will be appreciated that movement of the support 28 will result in some pivotal movement of the linkage arm 66 about its connection to the control arm 54, so that the through holes 64 at which the linkage arm 66 is connected to the second lever arm will tend to move slightly relative to the first lever arm.

Figure 6A:
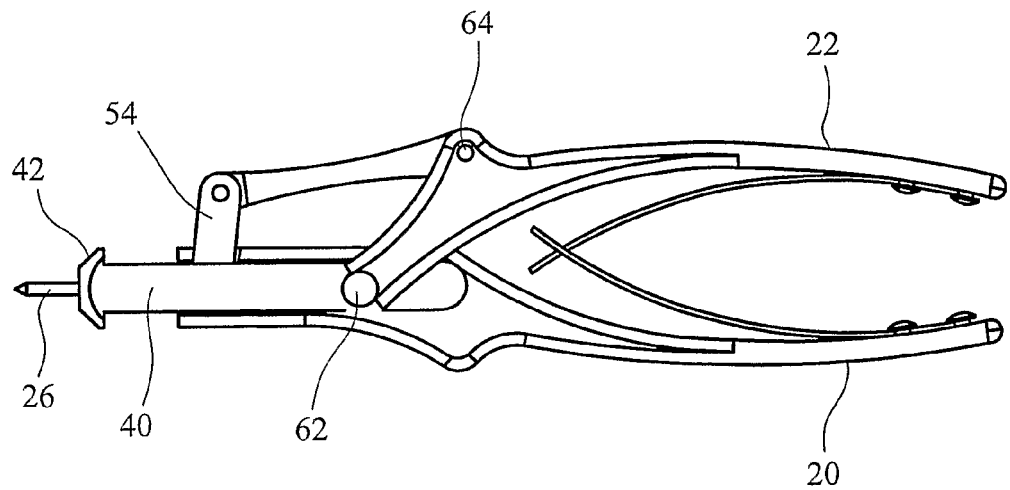
FIGS. 6A and 6B are side and sectional views respectively of the tool shown in FIG. 2, when the fixation pin has been at least partially extracted from a substrate by means of the tool.
Figure 6B:
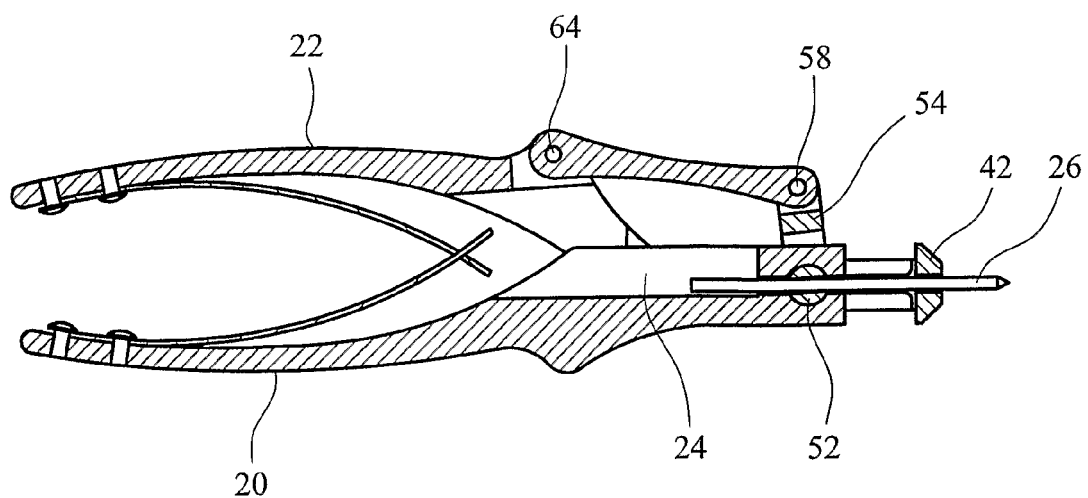

The result of the continued squeezing together of the first and second lever arms 20, 22 is shown in FIGS. 6a and 6b. As shown in these drawings, the fixation pin has been extracted at least partially from the bone or other substrate. Partial extraction using the tools of the present invention will often be sufficient to loosen the fixation pin so that it can then be slid out of the substrate completely. If the fixation pin has not been loosened sufficiently to enable it to be extracted completely, other than with the application of significant pulling force, the first and second lever arms can be opened (as shown in FIG. 5a). The tool can then be slid along the fixation pin. The first and second lever arms 20, 22 can then be squeezed together to repeat the sequence which has been described above with reference to FIGS. 5 and 6.

The invention claimed is:

1. A tool for extracting a pin having a free end from a substrate, the tool comprising:
   a first lever arm including a body part, the body part having a bore and a cavity communicating with the bore, the bore and the cavity being configured to receive at least a portion of the free end of the pin;
   a second lever arm pivotably connected to the first lever arm, the first lever arm and the second lever moveable between at least a first configuration, whereat the first lever arm and the second lever arm are separated by a first distance, and a second configuration, whereat the first lever arm and the second lever arm are separated by a second distance, the second distance being less than the first distance;

a linkage arm having a first end and a second end, the second end pivotably connected to the second lever arm;

a control arm having a free end and an opposite end, the free end pivotably connected to the first end of the linkage arm to pivotably connect the control arm to the second lever arm, and a jaw component extending from the opposite end of the control arm, the jaw component having a circular cross-section and being sized to be at least partially disposed and pivot within the cavity of the body part, the jaw component having a jaw bore and being pivotable between an unlocked position wherein the jaw bore and bore of the body part are aligned to receive a portion of a pin, when the first lever arm and the second lever arm are in the first configuration, and a locked position wherein the jaw component is pivoted to a position wherein the orientation of the jaw bore is changed so that the ends of the bore impart a localized bending force to a pin in the jaw component, when the first lever arm and the second lever arm are in the second configuration so that the jaw component engages the pin to substantially prevent the pin from sliding within the jaw bore when the jaw component is at the locked position; and a support pivotably attached to the second arm and slidably attached to the body part and slidable between a first position relative to the jaw component, when the first lever arm and the second lever arm are in the first configuration, and a second position more distal than the first position, when the first lever arm and the second lever arm are in the second configuration, the support including an end wall having an opening aligned with the bore of the body part.

2. The tool of claim 1, wherein the support comprises a first limb and a second limb extending from the end wall, each of which extend along opposite sides of the body part, the second lever arm being pivotably connected to the first limb and the second limb.

3. The tool of claim 1, wherein the jaw component is displaced within the cavity when the first lever arm and the second lever arm are moved from the first configuration to the second configuration.

4. The tool of claim 1, wherein the first lever arm and the second lever arm are configured such that the angle between the direction in which force is applied to the control arm to actuate the jaw component, and the direction in which force is applied to the support to cause the support to slide relative to the body part, is at least about 130°.

5. The tool of claim 1, wherein the support slides from the first position to the second position only when the first lever arm and the second lever arm are in the second configuration.

6. The tool of claim 1, wherein the body part is integral with the first lever arm.

7. The tool of claim 1, wherein the jaw component is configured to fit within the cavity in the body part such that the jaw component can be rotated within the cavity in a plane that contains the jaw bore.

* * * * *